United States Patent [19]

Rudek

[11] Patent Number: 4,498,049

[45] Date of Patent: Feb. 5, 1985

[54] RADIATION COMPENSATOR FOR GAS SENSORS

[75] Inventor: Fred Rudek, Mission Viejo, Calif.

[73] Assignee: Exo Sensors, Inc., Laguna Hills, Calif.

[21] Appl. No.: 357,309

[22] Filed: Mar. 11, 1982

[51] Int. Cl.³ ............................................ G01N 27/02
[52] U.S. Cl. .................................. 324/443; 204/401;
204/412; 204/415; 204/431; 376/256
[58] Field of Search ............... 324/443, 464; 204/1 T,
204/412, 415, 431, 401; 376/256; 73/23

[56] References Cited

U.S. PATENT DOCUMENTS

| | | | |
|---|---|---|---|
| 3,028,317 | 4/1962 | Wilson et al. | 204/431 |
| 3,149,921 | 9/1964 | Warner | 429/13 |
| 3,445,757 | 5/1969 | Krucoff | 324/464 |

*Primary Examiner*—Michael J. Tokar
*Assistant Examiner*—Kevin D. O'Shea
*Attorney, Agent, or Firm*—Blakely, Sokoloff, Taylor & Zafman

[57] ABSTRACT

A compensator device for providing direct and automatic correction of electrolytic gas sensor performance anomalies caused by exposure of the sensor to high levels of ionizing radiation. The compensator device, which compensates for changes in sensor performance while operating in a radiation field, provides an electromotive force which directly cancels that portion of the electromotive force developed by the active electrolytic gas sensor produced by the radiation rather than by presence of the gas. The compensating device is constructed in the same configuration as the active electrolytic sensor with the exception that the sensing electrode of the compensating device is not exposed to the sample gas environment. The sensor and compensator device are connected in a circuit such that their electromotive forces oppose one another, thereby determining the difference between the signals so that the radiation induced component is removed, and only the signal representing the partial pressure of gas remains. An alternate embodiment wherein the compensating signal is generated within the same sensor housing by the addition of one more electrode is also disclosed.

16 Claims, 6 Drawing Figures

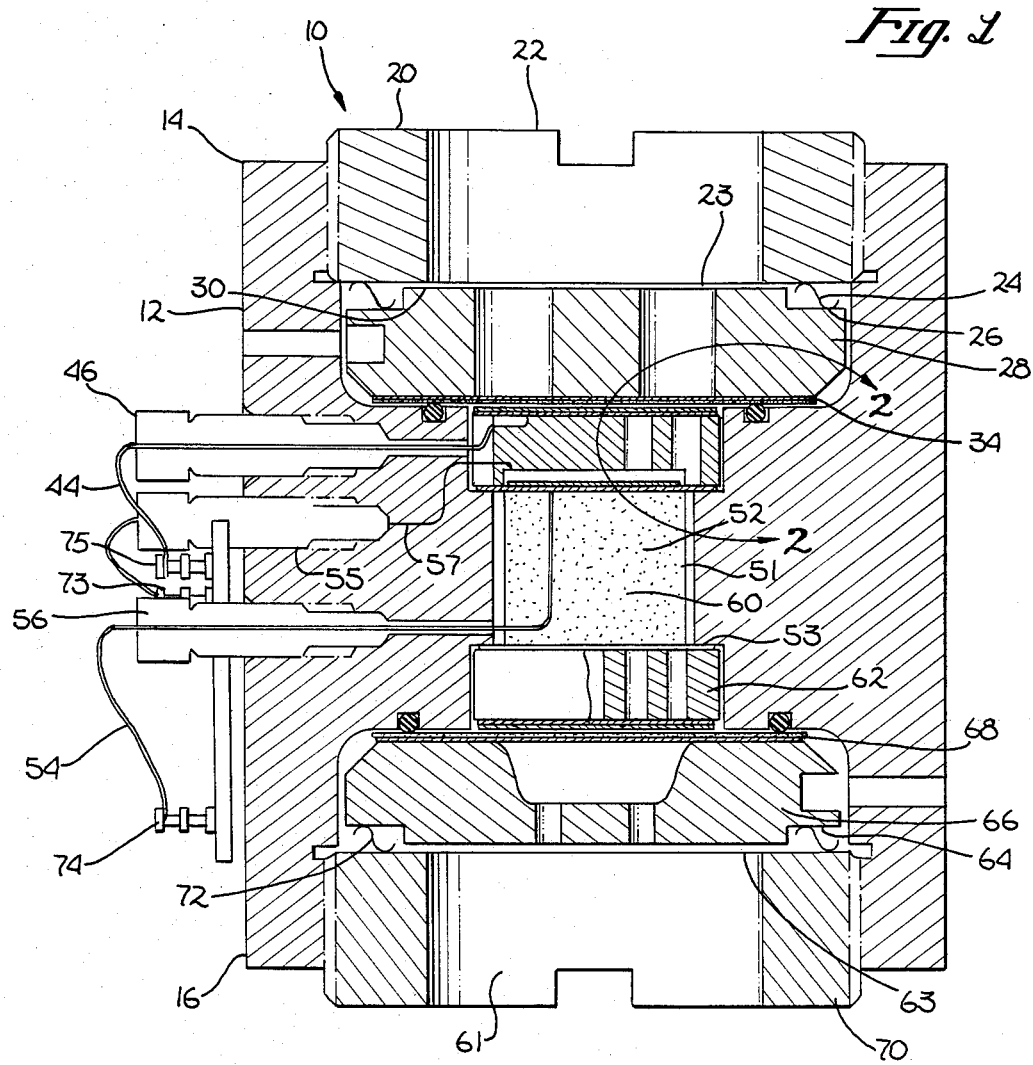
Fig. 1
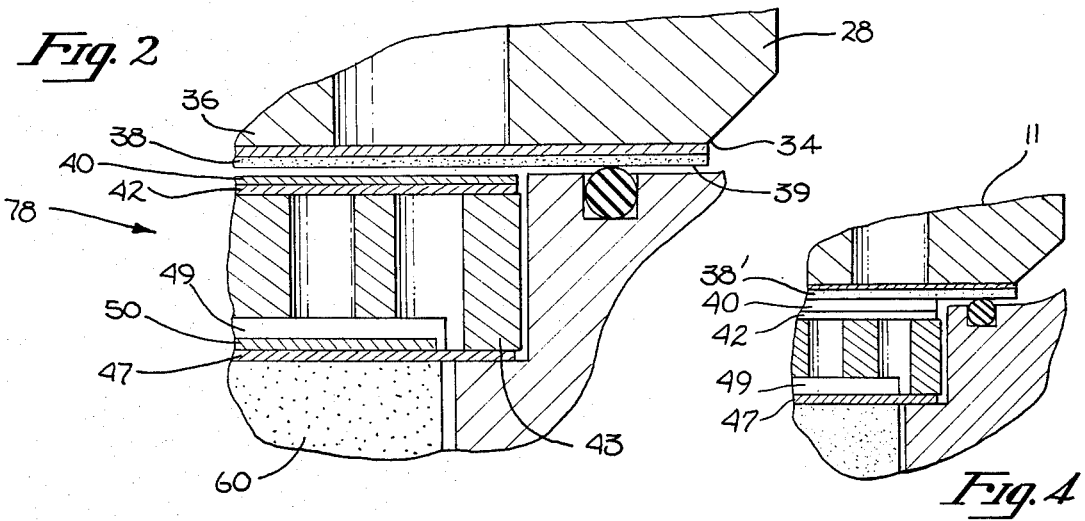
Fig. 2
Fig. 4

RADIATION COMPENSATOR FOR GAS SENSORS

BACKGROUND OF THE INVENTION

1. Field of the Invention

This invention relates to galvanic gas sensors and in particular, compensation networks for such sensors.

2. Description of the Prior Art

Galvanic gas sensors and similar devices are well known in the art. U.S. Pat. No. 3,149,921, to Warner, describes the basic technique of employing a fuel cell to measure partial pressures of a reactant gas, by arranging the various other cell conditions so that the cell electrical output is determined by the concentration of the reactant gas. This patent employs numerous techniques for producing electricity from cells by utilizing reactant gases as fuels and oxygens.

An improved gas sensor is disclosed in U.S. Pat. No. 3,616,411 issued to the present inventor, Rudek, into which an entering gas, metered by passage through a diffusion barrier, is ionized by contact with an absorbing catalyst in presence of an electrolyte. This ionization is representative of the partial pressure of the gas.

Since the prior art sensors are usually utilized in environments which produce many anomalies, the output signals appearing across the terminals of the gas sensors will not only represent the partial pressure of the gas being detected, but also will include a component which is environmentally induced. Therefore, a gas sensor which compensates for these environmentally induced anomalies would be of great advantage in the art.

SUMMARY OF THE INVENTION

In the present invention, a compensator device is provided which can be used to compensate for environmentally induced anomalies.

The compensator is comprised of a housing disposed within a hydrogen gas, having a sensing electrode and a counter electrode for generating an electrical potential therebetween indicative of the partial pressure of the gas to be detected including a component induced by the environmental anomalies. A third electrode is installed within the sensor which is electrically isolated from the outer two electrodes and isolated from the gas to be detected. The third electrode is connected to either the counter electrode or the sensing electrode such that the electric potential that is generated is a result of the environmentally induced anamoly. The signals from each electrode pair are connected to produce a difference in the signals, such that the output will be indicative of the partial pressure of the gas to be detected.

An alternate embodiment of the invention is disclosed which when connected with a typical gas sensor, such as is disclosed in the prior art, will produce an output signal representative of the partial pressure of the gas to be detected. In this embodiment, the electrodes are isolated from the gas such that the compensator provides an electromotive force which directly cancels the portion of the electromotive force caused by the environmentally induced anomaly.

BRIEF DESCRIPTION OF THE DRAWINGS

FIG. 1 is a cross-sectional view of the compensation sensor of the present invention.

FIG. 2 is the detailed view taken along lines 2—2 of the sensor in FIG. 1.

FIG. 4 is an alternate embodiment of a compensation sensor as shown in FIG. 2.

DETAILED DESCRIPTION OF THE INVENTION

Figure 5:
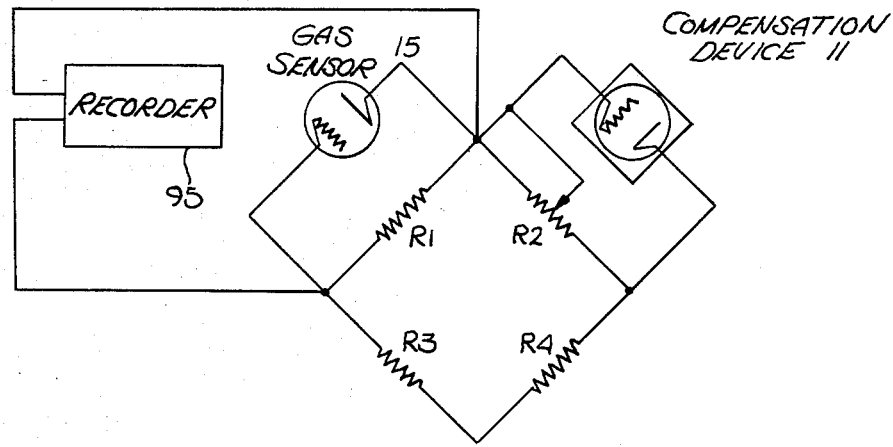
FIG. 5 is a schematic circuit diagram of the electrical interconnection between the compensation sensor of FIG. 4 and a typical gas sensor to effect compensation for environmentally induced anomalies in the output of the gas sensor.

In FIGS. 1 and 2, an electrolytic compensator 10 comprises a cylindrical housing 12 having first and second ends 14 and 16 respectively. Within end 14 and extending thereabove is a threaded annular retainer 20 having an axial passageway 22 and a lower end 23. Juxtaposed to retainer end 23 is cylindrical membrane retainer 28 having a shoulder 26 and upper and lower ends 30 and 34 respectively. Wave spring 24 is seated on shoulder 26 such that when retainer 20 is screwed clockwise, the spring 24 will compress and bring end 23 closer to end 30. End 34 rests upon membrane support side 36 of semipermeable membrane 38. The lower side 39 of membrane 38 rests against sensing electrode 40. Electrode 40 is placed upon electrode pad 42 and connected to a terminal post 75 by a wire 44 fed through compression screw 46.

Electrode pad 42 rests upon an inner electrode support 43. Support 43 is a polysufone wafer having holes containing electrolytic solution which are connected to a recess 49. During assembly, the recess provides an area for the electrolyte to flow. Within recess 49 is an electrode 50 resting on electrode pad 47. Support 43 provides support for the sensing electrode 40 from the inside, and seals electrode pad 47 at the edges to keep electrode 50 and sensing electrode 40 apart. Electrode 50 is connected to a terminal post 73 by a wire 57 that feeds through compression screw 55. Electrode pad 47 rests atop counter electrode assembly 60 which contains the counter electrode. Assembly 60 has a current collector screen 51 covered by a powder 52, which may be platinum dioxide ($PtO_2$), which are all immersed in an aqueous electrolyte solution. The powder is in intimate contact with screen 51 which is connected to terminal post 74 by a wire 54 fed through screw 56. The powder on current collector screen 51 forms a counter electrode 52. At the bottom of assembly 60 is electrode pad 53 which prevents migration of the counter electrode powder. Electrode pad 53 rests upon counter electrode retainer 62 which is a perforated, threaded polysulfone cap. Electrode retainer 62 rests upon bladder 68 which rests against expansion chamber ring 66. The bladder provides a means of compensating for the electrolyte expansion caused by environmental heating and references the internal volume to ambient pressure to minimize the pressure differentials across the seals.

Within end 16 of sensor 10 and extending therebelow is a second threaded annular retainer 70 having an axial passageway 61 and an upper end 63. Juxtaposed to retainer end 63 is the expansion chamber ring 66 having a shoulder 64. Wave spring 72 is seated within the shoulder 64 such that when retainer 70 bears against it, the spring 72 will compress.

Electrode 40 forms one half of a galvanic cell 78. The other half of cell 78 consists of the counter electrode assembly 60. When the diffusion of hydrogen to the sensing electrode 40 is restricted by diffusion membrane 38, the galvanic cell becomes "the sensor." All other mechanical components in the compensator 10 maintain the isolation between the sensing electrode 40 and the counter electrode 51 and also contain the electrolytic solution.

The cell 74 operates as a hydrogen or oxygen fueled battery. Hydrogen diffuses through the membrane 38 and is adsorbed on the sensing electrode 40. In the presence of the electrolytic solution, the adsorbed hydrogen is converted to an ion with a concurrent release of electrons. The electrons are picked up by the sensing electrode 40, carried outside the sensor housing via the wire 44 passed through the screw 46, through a thermistor network such as in FIG. 3, to the counter electrode current collector assembly 60, then to the counter electrode 52. All the internal components other then the electrodes and current collectors are electrically isolated from electron flow, but are all in contact with the sulfuric acid electrolytic solution which will conduct current (i.e. positive ions). Hydrogen ions are conducted through the electrolytic solution to the counter electrode 52. At the counter electrode, the reactants combine to form water and probably a combination of a lower form of platinum oxide and platinum. Since the electron source is the hydrogen gas, the current generated is a direct measure of the quantity of hydrogen reacted. The quantity of hydrogen reaching the sensing electrode is controlled by the rate of diffusion through the membrane, which is a function of the hydrogen partial pressure in the atmosphere. Hence, the current measured is the hydrogen partial pressure.

Figure 3:
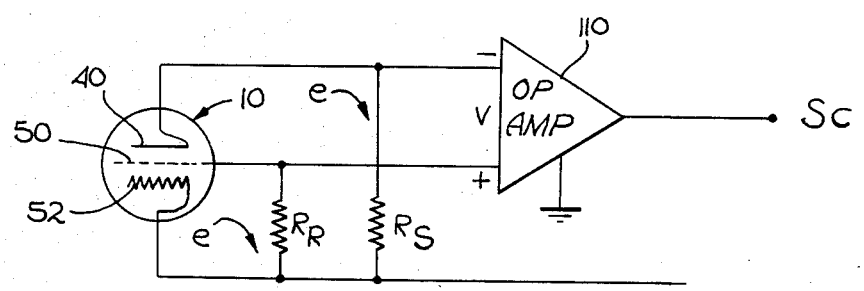
FIG. 3 is a schematic circuit diagram of the electrical connections made between the three electrodes of FIG. 1.

Electrode 50 may be electrically connected with sensing electrode 40 or counter electrode 52 as shown in FIG. 3. $R_R$ and $R_S$ are thermistors coupled to the positive and negative inputs of op amp 110 respectively. The output between sensing electrode 40 and counter electrode 52 will result from hydrogen and environmentally induced anomalies. All of the hydrogen diffused through the membrane 38 is used up (converted to H+) on the sensing electrode 40. The output between the electrode 50 and the counter electrode 52 can only be caused by something other than the hydrogen, which, for example, may be radiation. The output from each electrode pair are opposing and thereby cancel the non-hydrogen induced signal. The resulting compensated signal represents the hydrogen induced signal only.

In FIG. 4, a compensation device 11, similar to that of the above described compensator, is illustrated except that in this alternate embodiment, the semipermiable membrane 38 is replaced with a solid barrier member 38' which inhibits electron flow. In this embodiment, the third electrode 50 is not necessary. The gas whose partial pressure is being measured will not reach the counter electrode due to barrier member 38' and no reaction will occur. Therefore, the output of the compensation device will be due to environmental anomalies.

In operation, the alternate embodiment of the compensator device is connected to a typical gas sensor such as the one disclosed in U.S. Pat. No. 3,616,411 by this inventor in an electrical circuit. Both the gas sensor and compensator device 11 are subjected to the same environment, so the output signal of the gas sensor represents the combined output of the partial pressure of the gas and the anomalies caused by the environment. The output of the compensator device 11 represents only the output caused by radiation. The circuit takes the difference of the two output signals. The environmentally induced output of the compensator device will be subtracted from the output of the typical gas sensor. The only component remaining in the output signal of the combined sensor circuit is that portion representative of the partial pressure of the gas. Thus, the partial pressure of the gas can accurately be measured despite anomalies produced in the gas sensor output signal as a result of the environment.

One circuit which can effect such a differencing of output signal, shown in FIG. 5, is a simple Wheatstone Bridge comprising resistor $R_1$, variable resistor $R_2$, and resistors $R_3$ and $R_4$. The typical gas sensor 15 is connected in parallel across $R_1$ with connections being made to the terminal post connected to the electrodes therein. The compensation device 11 is connected in parallel across variable resistor $R_2$. The output signal of the bridge is taken across $R_1$, and for test purposes is provided to a strip chart recorder 95. The variable resistor $R_2$ is adjusted such that the recorder reads zero volts when both the gas sensor and the compensation sensor are in a normal atmosphere. In this configuration the electromotive force ("EMF") produced by the compensation device 11 (due entirely to radiation) counters the EMF produced by the typical gas sensor and precisely cancels that portion of the output current of gas sensor produced by radiation. Such a circuit automatically corrects the gas sensor output for radiation induced anomalies and greatly expands the range of radiation levels within which the gas sensor may accurately measure partial pressure of a gas.

While the Wheatstone Bridge circuit of FIG. 5 is utilized in the preferred alternate embodiment of the invention, it is possible to utilize bridge circuits of other standard configurations.

Figure 6:
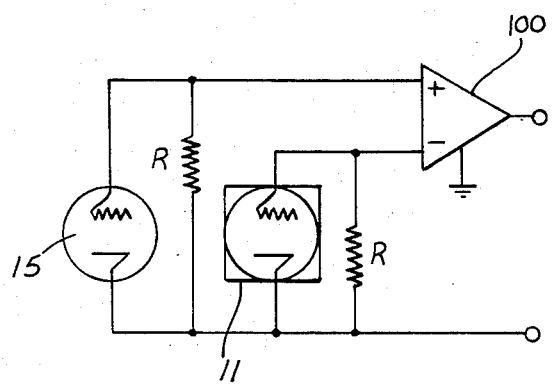
FIG. 6 is an alternate circuit diagram of the connections between the compensation sensor of FIG. 4 and a typical gas sensor to effect a compensated output signal.

FIG. 6 shows an alternate configuration of FIG. 5 for taking the difference in output signals of a typical gas sensor and the compensation device 11. Each sensor has its output signal impressed across a resistor. The output of the gas sensor 15 is applied to the positive input of a summing amplifier 100, and the output of the compensation device 11 is applied to the negative input of the summing amplifier 100. The output of the summing amplifier is then the difference of the two signals, i.e. the desired compensated output of the gas sensor.

The use of the compensator of the present invention inside nuclear power plants permits more effective monitoring of design basis accident. Prior to the availability of such compensator devices and circuits, the accepted procedure was to wait for some time (i.e. three to twenty four hours) before placing uncompensated gas sensors on line.

Obviously, while the invention has been disclosed and described with respect to a specific preferred embodiment thereof, it will be understood by those skilled in the art that various changes in form and detail may be made therein without departing from the spirit and scope of the invention.

I claim:

1. A device for detecting the partial pressure of a gas within an environment which produces anomalies, comprising:

housing means disposed within the gas;

first electrode means disposed within said housing means;

second electrode means disposed within said housing means;

first connection means coupling said first electrode means to said second electrode means producing a first electrical potential indicative of the partial pressure of the gas to be detected including any environmentally induced anomalies;

third electrode means dispose within said housing means electrically isolated from said first and second electrode means and isolated from the gas to be detected;

second connection means coupling said third electrode means to said first electrode means producing a second electrical potential indicative of environmentally induced anomalies;

whereby when said second potential is subtracted from said first potential, a signal representative of the partial pressure of the gas will be produced.

2. The device of claim 1 further comprising a circuit for subtracting said second potential from said first potential.

3. The device of claim 1 wherein said first electrode means and said second electrode means are coupled to form a galvanic cell.

4. A device for detecting the partial pressure of a gas within an environment which produces anomalies, comprising:

a gas sensor disposed within the gas having sensing electrode means and counter electrode means which when coupled together generate a first electrical potential indicative of the partial pressure of the gas to be detected including any environmentally induced anomalies, and third electrode means isolated from said sensing and counter electrode means, said third electrode means being electrically coupled to one of said electrode means to generate a second electrical potential indicative of environmentally induced anomalies;

whereby when said second potential is subtracted from said first potential, a signal representative of the partial pressure of the gas will be produced.

5. The device of claim 4 further comprising a circuit for subtracting said second potential from said first potential.

6. The device of claim 4 wherein said third electrode means is coupled to said sensing electrode means.

7. The device of claim 4 wherein said third electrode means is coupled to said counter electrode means.

8. The device for detecting the partial pressure of the gas within an environment which produces anomalies, comprising:

cylindrical housing means having a first and a second end;

annular retainer means having an axial passageway and a lower end disposed within the first end of said cylindrical housing means;

cylindrical membrane retainer means disposed proximate to said lower end of the annular retainer means;

semipermeable membrane means juxtapositioned to said cylindrical membrane retainer means;

sensing electrode means resting against said semipermeable membrane means connected to a first terminal means;

second electrode means electrically isolated from said sensing electrode means connected to second terminal means, said second terminal means being coupled to said first terminal means;

third terminal means connected to said first terminal means;

current collector assembly means covered by a powder which is connected to said third terminal means;

whereby when said first terminal means is connected to said third terminal means a first potential indicative of the partial pressure of the gas detected including any environmentally induced anomalies will be produced, and when said second terminal is coupled to said first terminal means, a second potential indicative of environmentally induced anomalies will be produced, such that when said second potential is subtracted from said first potential, a signal representative of the partial pressure of the gas will be generated.

9. The device of the proceeding claim 8 further comprising a circuit for subtracting said second potential from said first potential.

10. The device for operating with an environment containing anomalies for generating an output signal indicative of the presence of a gas detected, comprising;

a gas sensor disposed within said gas to be detected, having sensing electrode means and counter electrode means, said sensor providing a first output signal;

a compensation sensor having a counter electrode means and sensing electrode means, said sensing electrode being isolated from said gas to be detected, said compensation sensor providing a second output signal;

whereby when said second output signal is subtracted from said first output signal, the resulting signal is representative of the partial pressure of the gas to be detected.

11. The device according to claim 10 further comprising differentiating means for taking the difference between said second output signal and said first output signal.

12. The device according to claim 11 wherein said means comprises a circuit having a Wheatstone bridge connected to a recording means.

13. The device according to claim 12 wherein said Wheatstone bridge comprises:

a first resistance connected across the output of said gas sensor;

a variable resistance connected across the output of said compensation sensor;

a third resistance connected to said sensing electrode means of said gas sensor;

a fourth resistance connected to said sensing electrode means of said compensation sensor, wherein said third resistance and said fourth resistance are connected together;

whereby said output signal is measured across said first resistance by said recording means.

14. The device according to claim 11 wherein said differentiating means comprises a summing amplifier.

15. The device for detecting the partial pressure of the gas within an environment which produces anomalies, comprising:

cylindrical housing means having a first and a second end;

an annular retainer means having an axial passageway and a lower end disposed within the first end of said cylindrical housing means;

cylindrical membrane retainer means disposed proximate to said lower end of the annular retainer means;

semipermeable membrane means juxtapositioned to said cylindrical membrane retainer means;

sensing electrode means resting against said semipermeable membrane means connected to a first terminal means;

second electrode means electrically isolated from said sensing electrode means connected to second terminal means;

third terminal means connected to said first terminal means and said second terminal means;

current collector assembly means covered by a powder which is connected to a third terminal means;

whereby when said first terminal means is connected to said third terminal means a first potential indicative of the partial pressure of the gas detected including any environmentally induced anomalies will be produced, and when said second terminal is coupled to said third terminal means, a second potential indicative of environmentally induced anomalies will be produced, such that when said second potential is subtracted from said first potential, a signal representative of the partial pressure of the gas will be generated.

16. The device of the proceeding claim 15 further comprising a circuit for subtracting said second potential from said first potential.

* * * * *